United States Patent [19]

Harvey

[11] Patent Number: 5,023,345

[45] Date of Patent: Jun. 11, 1991

[54] PREPARATION OF ALKYLENE CARBONATES

[75] Inventor: Robert J. Harvey, Teaneck, N.J.

[73] Assignee: Scientific Design Company, Inc., Little Ferry, N.J.

[21] Appl. No.: 327,126

[22] Filed: Mar. 22, 1989

Related U.S. Application Data

[60] Division of Ser. No. 502,024, Jun. 7, 1983, Pat. No. 4,841,072, which is a continuation of Ser. No. 326,447, Dec. 2, 1981, abandoned.

[51] Int. Cl.$^5$ ............................................. C07D 317/12
[52] U.S. Cl. ..................................................... 549/230
[58] Field of Search ......................................... 549/230

[56] References Cited

U.S. PATENT DOCUMENTS

| | | | |
|---|---|---|---|
| 2,667,497 | 1/1954 | Cline | 549/230 |
| 2,773,070 | 12/1956 | Lichtenwalter et al. | 549/230 |
| 2,994,704 | 8/1961 | Crosby et al. | 549/230 |
| 2,994,705 | 8/1961 | Crosby et al. | 549/230 |
| 3,629,343 | 12/1971 | Levin et al. | 568/867 |
| 3,922,314 | 11/1975 | Cocuzza et al. | 568/867 |
| 4,160,116 | 7/1979 | Mieno et al. | 568/867 |
| 4,233,221 | 11/1980 | Raines et al. | 549/230 |

FOREIGN PATENT DOCUMENTS

| | | |
|---|---|---|
| 55-122776 | 9/1980 | Japan. |
| 56-45426 | 4/1981 | Japan. |
| 1485925 | 9/1977 | United Kingdom. |

*Primary Examiner*—C. Warren Ivy
*Assistant Examiner*—Amelia A. Owens
*Attorney, Agent, or Firm*—Kenneth H. Johnson

[57] ABSTRACT

Alkylene carbonates, particularly ethylene carbonate, are prepared by the reaction of an alkylene oxide with carbon dioxide in the presence of a catalyst at temperatures in the region of the critical temperature of carbon dioxide, preferably 25°–70° C. and at autogenerated pressures, typically 30 to 200 kg/cm$^2$ gauge. The conversion of alkylene oxide to alkylene carbonate can be carried out in the presence of water while minimizing the undesirable hydrolysis of the carbonate to athe corresponding alkylene glycol. With certain catalysts the presence of water improves the selectivity to the formation of the carbonate.

9 Claims, No Drawings

PREPARATION OF ALKYLENE CARBONATES

This Application is a division of Ser. No. 502,024 filed Jun. 7, 1983 now U.S. Pat. No. 4,841,072 which was a continuation of Ser. No. 326,447 filed Dec. 2, 1981, now abandoned.

PRIOR ART

The invention relates to a process for the preparation of alkylene carbonates by the reaction of the corresponding alkylene oxide with carbon dioxide. Such reactions are well known in the art. Alkylene carbonates are useful as solvents or as a source of the corresponding glycols. They are of particular interest as intermediates in the process of converting ethylene oxide into ethylene glycol while avoiding the inefficiency associated with the conventional hydration process.

Several processes have been disclosed for a single step hydration of alkylene oxides to glycols in the presence of a catalyst and carbon dioxide. Such processes are said to make possible the reduction in the amount of water used. The removal of excess water is a major expense in the conventional hydration process. The carbon dioxide is not consumed in the process, but it has been suggested that the hydration proceeds via the alkylene carbonate as an intermediate compound.

U.S. Pat. No. 3,922,314 discloses a process for the hydration of ethylene oxide to ethylene glycol which uses no catalyst, but operates with an aqueous ethylene oxide solution containing at least 8 wt % ethylene oxide and at least 0.1 wt % carbon dioxide.

A catalytic process is described in British patent 1,177,877 (or U.S. Pat. No. 3,629,343). Alkylene oxides are hydrated to the glycols at temperatures of 80°–220° C. and pressures of 10–180 atmospheres in the presence of a halide catalyst. Preferred are alkali metal or quaternary ammonium halides, particularly bromides and iodides. Alkali metal hydroxides, carbonates, or bicarbonates were said to be beneficial.

A similar process is discussed in U.S. Pat. No. 4,160,116 where quaternary phosphonium halides, preferably the iodides and bromides were used to catalyze the hydration of alkylene oxides in the presence of carbon dioxide. The temperature is 50°–200° C. and the pressure 3–50 kg/cm$^2$.

Still another such process is disclosed in published Japanese patent application 81-45426, in which molybdenum and/or tungsten compounds are combined with known catalysts such as alkali metal halides, quaternary ammonium or phosphonium salts, organic halides, and organic amines. The reaction is stated to be carried out at 20°–250° C. and 0–30 kg/cm$^2$ gauge.

The formation of alkylene carbonates, as opposed to the hydration of alkylene oxides to glycols, takes place in the prior art to be discussed with no water present. Catalysts and reaction conditions similar to those described above for the hydration of alkylene oxides have been disclosed to be useful.

In U.S. Pat. No. 2,667,497 magnesium or calcium halides were used at 150°–250° C. and 500–2000 psi to produce alkylene carbonates from the corresponding oxides.

U.S. Pat. No. 2,766,258 discloses the use of quaternary ammonium hydroxides, carbonates, and bicarbonates to catalyze the reaction of alkylene oxides with carbon dioxide. The reaction was carried out at temperatures between 100°–225° C. and pressures of 300–500 psig.

The quaternary ammonium halides were used by the patentees in U.S. Pat. No.2,773,070 at temperatures of 100°–225° C. and pressures greater than 800 psi.

Amines were the catalyst used for the reaction by the patentees in U.S. Pat. No. 2,773,881. The reaction was carried out at 100°–400° C. and more than 500 psi.

Three patents issued to the same assignee, i.e. U.S. Pat. Nos. 2,994,705; 2,994,704; and 2,993,908 disclose substantially the same conditions, 93°–260° C. and 8–212 kg/cm$^2$ gauge, with organic phosphonium halides, organic sulfonium halides, and urea hydrohalides given as catalysts for the preparation of alkylene carbonates from the corresponding oxirane compound.

Hydrazine or a halide salt thereof was used to catalyze the reaction by the patentees in U.S. Pat. No. 3,535,341 at temperatures of 100°–250° C. An anion exchange resin containing quaternary ammonium groups was disclosed in U.S. Pat. No. 4,233,221 as useful for vapor-phase reaction.

Organic antimony halides were shown in published Japanese patent application 80-122,776 to make possible the formation of alkylene carbonates, at room temperature to 120° C., in a water-free mixture. The time required in the single example carried out at room temperature was about 5 days, a generally impractical period of time.

I have now discovered that the reaction of alkylene oxides to the corresponding carbonates can be carried out with known catalysts at lower temperatures than heretofore used in the art. Further, the reaction is operable even in the presence of substantial amounts of water. The hydrolysis of the carbonates to glycols can be minimized and the principal product is the carbonate, as will be seen in the following discussion.

SUMMARY OF THE DISCLOSURE

Alkylene oxides may be reacted with carbon dioxide to form alkylene carbonates in the presence of a catalytic amount of suitable catalysts at relatively low temperatures in the range of about 20°–90° C. and in the presence of water. Preferably the temperature will be about 30°–70° C. The pressure at which the reaction is carried out is in the range of about 25–200 kg/cm$^2$ gauge, and may be autogenerated. The mol ratio of carbon dioxide to alkylene oxide is in the range of 1/1–100/1 and preferably about 2/1–10/1. Suitable catalysts include a member or members of the group consisting of quaternary organic ammonium and phosphonium halides, organic sulfonium halides, and organic antimony halides, particularly methyl triphenyl phosphonium iodide, tetra-ethyl ammonium bromide, and tetraphenyl antimony bromide. The corresponding carboxylates may also be used. The quantity of catalyst used is generally within the range of 0.01 to 0.15 mols per mol of alkylene oxide, preferably 0.02 to 0.10.

Contrary to previous expectations, water may be present in substantial amounts, even exceeding those used in prior art hydration processes, but without formation of significant amounts of glycol. Useful mol ratios of water to alkylene oxide are 0.1/1–20/1. With certain catalysts, the effect of water actually is to improve the selectivity of the conversion of the oxirane to the carbonate.

In another embodiment, the invention comprises a process for reacting alkylene oxides with carbon dioxide to form alkylene carbonates at relatively low temperatures in the range of about 20°–90° C. in the presence of at least one catalyst selected from the group consisting of quarternary organic ammonium and phosphonium halides and carboxylates and organic sulfonium halides and carboxylates. Such catalysts have hitherto been employed at operating temperatures higher than those now found to be useable.

DESCRIPTION OF THE PREFERRED EMBODIMENTS

Heretofore, those familiar with the reaction of alkylene oxides with carbon dioxide to form alkylene carbonates have carried out the reaction at temperatures generally in the range of 100°–300° C., particularly about 150°–225° C. Although it was not generally discussed in detail, it will be seen from prior art disclosures that the reaction was carried out in the practical absence of water. For Example, in U.S. Pat. No. 4,233,221 the reactants were dried by condensation of water after compression so that the moisture level of the reactant gases was quite low, estimated to be about 0.2 mol percent. Since the hydrolysis of carbonates was known to take place at elevated temperatures and with catalysts also useful for the direct hydrolysis of alkylene oxides to glycols, it seems probable that prior workers in the art avoided water if only the carbonate was to be produced. Otherwise, hydrolysis to the glycol could be expected.

Surprisingly, I have found that when the reaction of alkylene oxides with carbon dioxide is undertaken at temperatures substantially lower than taught by the prior art, that the presence of water can be not only tolerated, but actually may be beneficial in some instances. Alkylene carbonates can be prepared with minimal losses by hydrolysis to the glycols. This process is particularly useful when applied to a stream combining carbon dioxide, ethylene oxide, and water obtained by extraction of ethylene oxide from a dilute aqueous solution with near-critical or supercritical carbon dioxide.

The reaction may be carried out at temperatures in the range of about 20°–90° C., preferably 25°–80° C., especially 30°–70° C. Although lowering the temperature would be expected to increase the reaction time, nevertheless reasonable periods in the general range of 2–8 hours may be achieved by properly selecting the amount and type of catalyst and the other reaction conditions. In one embodiment, the temperature used is established by the ambient conditions available for cooling the feed mixture and thus would be in the range of about 20°–30° C.

Pressure is not an especially critical variable in the reaction. Typically, it will be in the range of about 25–200 kg/cm$^2$ gauge and if the temperature is sufficiently low, will be autogenerated and thus established by the feed composition and the temperature at which the reaction is carried out.

The molar ratio of carbon dioxide to alkylene carbonate may range from 1/1 to 100/1. Usually a ratio greater than 1/1 would be selected, preferably 2/1 to 10/1. Where the process of the invention is associated with the extraction of alkylene oxide by (near) super-critical carbon dioxide the ratio may be 40/1–60/1, with satisfactory results obtained.

It is of particular importance that water does not appear to hydrolyze alkylene carbonates to the glycols to a significant extent under conditions found suitable for the process of the invention. At higher temperatures, the amount of glycols produced would be expected to increase until eventually the process would no longer produce carbonates, but glycols, instead as disclosed in the patents mentioned earlier. No limit has been established on the amount of water which can be tolerated, in fact, amounts well in excess of those useful for the direct hydration of alkylene oxides to glycols have been demonstrated, as will be seen in subsequent examples. Remarkably, it has been discovered that the presence of water may have a beneficial effect on the selectivity of the reaction to produce carbonate, contrary to what might be expected. This effect may be more pronounced in association with certain catalysts, particularly those in which the bond between the halide atom and the rest of the molecule is ionic, rather than covalent in nature.

The catalysts found useful in the process of the invention include many of those known in the art, but used now under significantly altered conditions. Broad classes of compounds which may be useful include one or more members of the group consisting of organic quaternary ammonium or phosphonium halides organic sulfonium halides, and organic antimony halides. The corresponding carboxylates also may be used. Examples of compounds which may be employed are the following ammonium compounds tetraethyl ammonium bromide, and tetra ethyl ammonium iodide. Specific phosphonium compounds include methyl triphenyl phosphonium iodide and methyl triphenyl phosphonium bromide. Sulfonium compounds may include trimethyl sulfonium iodide and trimethyl sulfonium bromide. Antimony compounds have been found quite effective when no water is present, but appear to be adversely affected when water is included. Typical compounds are tetraphenyl antimony bromide and triphenyl antimony dichloride. Particularly preferred catalysts when water is present are methyl triphenyl phosphonium iodide and tetraethyl ammonium bromide. Of the halides, bromides and iodides are preferred.

The amount of catalyst will be similar to that used in other processes, about 0.01–0.15 mols of the catalyst per mol of alkylene oxide may be used, preferably 0.02–0.1 mols per mol, although larger or smaller amounts are not intended to be excluded.

While other workers in the field have indicated that relatively high temperatures of 100° C. or preferably more would be used either to form alkylene carbonates when no water was present, or alkylene glycols when water was available to hydrolyze alkylene oxides, it has been found that by carrying out the reaction at low temperatures in the range of about 20°–90° C., preferably 30°–70° C., one can produce alkylene carbonates and even in the presence of water.

The reaction to form carbonates may be carried out in the presence of substantial amounts of water. At higher temperatures typical of the prior art, glycols would be expected when water is present and, in fact, this is the basis for several processes as previously discussed. As will be seen, by operating at relatively low temperatures, it is possible to minimize hydrolysis and to form carbonates instead.

EXAMPLE 1

A sample of the catalyst being tested is introduced to a 130 cc bomb produced by the Parr Instrument Company. Samples of ethylene oxide and carbon dioxide are charged at −78° C. by immersing the bomb in a dry-ice/acetone bath. The bomb is then closed and placed in a 36° C. bath so that the internal temperature of the bomb is increased to 30° C. and the reaction proceeds. Agitation is via a magnetically driven disk. After a suitable period of time, the bomb is removed from the bath and the contents analyzed. The results of a number of such tests are shown in Table A below.

TABLE A

| Test No. | Feed, millimols | | Catalyst, gms*** | Bath °C. | Time, hrs | Max. Pressure kg/cm² gauge | EO* Conv. % | EC** Sel. % |
|---|---|---|---|---|---|---|---|---|
| | EO* | CO₂ | | | | | | |
| 1 | 13.6 | 681 | a 0.1456 | 36 | 19.5 | 28.1 | 51.7 | — |
| 2 | 13.6 | 681 | b 0.4385 | 36 | 19.5 | 29.5 | 55 | 16 |
| 3 | 18.2 | 681 | c 0.3654 | 32 | 19.5 | 18.3 | 94 | 88.2 |
| 4 | 15.9 | 681 | d 0.3064 | 37 | 18.5 | 15.5 | 37.7 | — |
| 5 | 18.2 | 1022 | e 0.3881 | 38 | 19.5 | 30.6 | 51.1 | — |
| 6 | 22.7 | 1022 | f 0.2406 | 38 | 19.5 | 78.1 | 77.9 | 50.4 |

*EO = ethylene oxide
**EC = ethylene carbonate
***a = trimethyl sulfonium iodide
b = methyl triphenyl phosphonium iodide
c = tetraphenyl antimony bromide
d = triphenyl antimony dichloride
e = methyl triphenyl phosphonium bromide
f = tetraethyl ammonium bromide It has been discovered that water may be present without formation of significant amounts of glycols, provided that the temperature is sufficiently low. Surprisingly, it has been found that water has a beneficial effect on the selectivity to the carbonate with some catalysts, while with others the selectivity appears to be suppressed.

EXAMPLE 2

Effect of Water on Catalysts

The procedure of Example 1 is followed except that varying amounts of water are introduced to the Parr bomb, with the following results.

TABLE B

| Test No. | Feed, millimols | | | Catalyst, gms* | Bath °C. | Time, hrs | Max. Pres. kg/cm2 gauge | EO Conv. % | EC Sel. % |
|---|---|---|---|---|---|---|---|---|---|
| | EO | CO2 | H2O | | | | | | |
| 7 | 19.3 | 1022 | — | c 0.5507 | 33 | 19.5 | 27.8 | 91.1 | 88.5 |
| 8 | 18.2 | 1022 | 10 | c 0.5466 | 34 | 19.5 | 27.4 | 95.6 | 47.1 |
| 9 | 20.4 | 1022 | 5 | b 0.4380 | 37 | 21 | 44.3 | 86 | 35 |
| 10 | 20.4 | 1022 | 20 | b 0.4227 | 37 | 21 | 42.5 | 92 | 47.4 |
| 11 | 20.4 | 1022 | 40 | b 0.4319 | 37 | 21 | 43.2 | 93 | 63 |
| 12 | 22.7 | 1022 | 80 | b 0.4365 | 37 | 21 | 41.1 | 83.8 | 76 |

*c = tetraphenyl antimony bromide
b = methyl triphenyl phosphonium iodide

The data of Table B show that the presence of water appears to have no recognizable effect on the overall conversion of ethylene oxide, the selectivity to ethylene carbonate is reduced when catalyst "c" is used, while when catalyst "b" is employed the selectivity to ethylene carbonate is surprisingly improved. Catalyst "c" would be more suitable for a reaction system in which the amount of water present is not large. Note that the ratio of water to ethylene oxide is about 0.55/1 compared to the theoretical ratio of 1/1 for the hydrolysis reaction. Catalyst "b" appears less effective when no water is present (see test 2) but its performance is enhanced when water is used. Note that the ratios for this catalyst shown reach nearly 4/1 water/EO.

Although the process of the invention is particularly useful in connection with the formation of ethylene carbonate, it is more widely applicable to other oxirane compounds, as will be seen in the following example.

EXAMPLE 3

A sample of the catalyst being tested and water (if used) is introduced to a 130 cc Parr bomb. Samples of propylene oxide and carbon dioxide are charged at −78° C. by immersing the bomb in a dry-ice/acetone bath. The bomb is then closed and placed in a 36° C. bath so that the internal temperature of the bomb is increased to 30° C. and the reaction proceeds. After a suitable period of time, the bomb is removed from the bath and the contents analyzed. The results of a number of such tests are shown in Table C below.

TABLE C

| Test No. | Feed, millimols | | | Catalyst, gms*** | Bath °C. | Time, hrs | Max. Pres. kg/cm2 gauge | PO Conv. % | PC** Sel. % |
|---|---|---|---|---|---|---|---|---|---|
| | PO* | CO2 | H2O | | | | | | |
| 13 | 20.3 | 1022 | — | a 0.5511 | 35 | 21 | 42.6 | 96.2 | 90.3 |
| 14 | 20.6 | 1022 | — | b 0.4385 | 36 | 21 | 34.2 | 60.2 | 25.4 |
| 15 | 20.2 | 1022 | — | c 0.2401 | 36 | 21 | 56.1 | 85.0 | 58.3 |
| 16 | 20.4 | 1022 | 5 | b 0.4382 | 36 | 21 | 47.3 | 88.2 | 34.6 |
| 17 | 20.6 | 1022 | 20 | b 0.4378 | 36 | 21 | 52.8 | 89.7 | 56.4 |
| 18 | 20.1 | 1022 | 40 | b 0.4386 | 36 | 21 | 54.2 | 87.4 | 68.3 |
| 19 | 20.4 | 1022 | 80 | b 0.4391 | 36 | 21 | 62.1 | 91.4 | 82.3 |

*PO = propylene oxide
**PC = propylene carbonate
***a = tetraphenyl antimony bromide
b = methyl triphenyl phosphonium iodide
c = tetraethyl ammonium bromide

EXAMPLE 4

The experimental procedure of Example 3 was followed with 1,2-butylene oxide charged in lieu of propylene oxide. The results of a number of such tests are shown in Table D below.

TABLE D

| Test No. | Feed, millimols BO* | CO2 | H2O | Catalyst, gms*** | Bath °C. | Time, hrs | Max. Pres. kg/cm2 gauge | BO Conv. % | BC** Sel. % |
|---|---|---|---|---|---|---|---|---|---|
| 20 | 20.4 | 1022 | — | a 0.5513 | 36 | 21 | 44.8 | 92.1 | 87.6 |
| 21 | 20.7 | 1022 | — | b 0.4378 | 36 | 21 | 47.2 | 58.3 | 22.6 |
| 22 | 20.1 | 1022 | — | d 0.2436 | 36 | 21 | 42.6 | 82.0 | 53.2 |
| 23 | 20.1 | 1022 | 5 | b 0.4386 | 36 | 21. | 51.8 | 89.2 | 40.5 |
| 24 | 20.8 | 1022 | 20 | b 0.4392 | 36 | 21 | 43.8 | 91.4 | 59.8 |
| 25 | 20.2 | 1022 | 40 | b 0.4369 | 36 | 21 | 56.2 | 93.4 | 72.8 |
| 26 | 20.6 | 1022 | 80 | b 0.4381 | 36 | 21 | 53.6 | 90.8 | 84.3 |

*BO = 1,2-butylene oxide
**BC = 1,2-butylene carbonate
***a = tetraphenyl antimony bromide
b = methyl triphenyl phosphonium iodide
c = tetraethyl ammonium bromide

EXAMPLE 5

A sample of the catalyst being tested, along with $H_2O$ and solvents (when used) is introduced to a 300 cc electrically heated stainless steel autoclave equipped with impeller agitation produced by Autoclave Engineers, Inc. Samples of ethylene oxide and carbon dioxide are charged at −78° C. while the autoclave is immersed in a dry-ice/acetone bath. The autoclave is then closed and heated to the desired reaction temperature. After a suitable period of time, the autoclave is cooled and the contents analyzed. The results of a number of such tests are shown in Table E below.

TABLE E

| Test No. | Feed, millimols EO* | CO$_2$ | H$_2$O | THF** | Catalyst, gms*** | Bath °C. | Time, hrs | Max. Pres. kg/cm$^2$ gauge | EO Conv. % | EC**** Sel. % |
|---|---|---|---|---|---|---|---|---|---|---|
| 27 | 347 | 1590 | 346 | 1262 | a 20.0 | 60 | 4 | 52.0 | 95.6 | 97.0 |
| 28 | 695 | 2794 | 695 | — | a 20.0 | 60 | 6 | 104.8 | 95.8 | 90.5 |
| 29 | 1157 | 2113 | 583 | — | a 20.0 | 50 | 6 | 57.7 | 98.2 | 95.5 |
| 30 | 349 | 1590 | 350 | 1263 | a 20.0 | 70 | 2 | 57.3 | 99.5 | 96.0 |

*EO = ethylene oxide
**THF = tetrahydrofuran
***a = methyl triphenyl phosphonium iodide
****EC = ethylene carbonate

What is claimed:

1. A process for preparing alkylene carbonates by the reaction of an alkylene oxide with carbon dioxide in the presence of at least one catalyst selected from the group consisting of organic quaternary ammonium halides, and organic sulfonium halides, at a temperature in the range of 20°–90° C.

2. The process of claim 1 wherein the temperature is in the range of 30°–70° C.

3. The process of claim 1 wherein the pressure is in the range of about 25–200 kg/cm$^2$ gauge.

4. The process of claim 1 wherein said catalyst is trimethyl sulfonium iodide.

5. The process of claim 1 wherein said catalyst is tetraethyl ammonium bromide.

6. The process of claim 1 wherein said catalyst is present in a ratio of 0.01 to 0.15 ml per mol of alkylene oxide.

7. The process of claim 1 wherein the mol ratio of carbon dioxide to alkylene oxide is in the range of about 1/1 to 100/1.

8. The process of claim 6 wherein said mol ratio is about 2/1 to 10/1.

9. The process of claim 1 wherein said alkylene oxide is ethylene oxide.

* * * * *